United States Patent
Garcia-Olmo et al.

(10) Patent No.: US 9,555,075 B2
(45) Date of Patent: Jan. 31, 2017

(54) METHOD FOR BLOCKING TUMOUR GROWTH

(71) Applicant: The Foundation for Biomedical Research of La Paz University Hospital (FIBHULP), Madrid (ES)

(72) Inventors: Damián Garcia-Olmo, Madrid (ES); Mariano Garcia-Arranz, Madrid (ES); Luz Vega Clemente, Madrid (ES); Peter Brian Gahan, London (GB); Maurice Stroun, Geneva (CH)

(73) Assignee: THE FOUNDATION FOR BIOMEDICAL RESEARCH OF LA PAZ UNIVERSITY HOSPITAL (FIBHULP), Madrid (ES)

( * ) Notice: Subject to any disclaimer, the term of this patent is extended or adjusted under 35 U.S.C. 154(b) by 24 days.

(21) Appl. No.: 14/290,094

(22) Filed: May 29, 2014

(65) Prior Publication Data
US 2015/0071986 A1    Mar. 12, 2015

(30) Foreign Application Priority Data

May 29, 2013   (EP) .................................... 13169783

(51) Int. Cl.
| | | |
|---|---|---|
| *A61K 38/02* | (2006.01) | |
| *A61K 38/17* | (2006.01) | |
| *A61K 35/12* | (2015.01) | |
| *A61K 35/54* | (2015.01) | |
| *A61K 35/407* | (2015.01) | |
| *A61K 9/127* | (2006.01) | |
| *A61K 9/51* | (2006.01) | |
| *A61K 35/17* | (2015.01) | |
| *A61K 35/545* | (2015.01) | |

(52) U.S. Cl.
CPC ........... *A61K 38/1709* (2013.01); *A61K 9/127* (2013.01); *A61K 9/51* (2013.01); *A61K 35/17* (2013.01); *A61K 35/407* (2013.01); *A61K 35/545* (2013.01); *A61K 2035/124* (2013.01)

(58) Field of Classification Search
None
See application file for complete search history.

(56) References Cited

PUBLICATIONS

Viola-Magni et al (Journal of Nucleic Acids Investigation, 2011, vol. 2, suppl. 1, p. 10).*
Viola-Magni et al (Journal of Nucleic Acids Investigation, 2011, vol. 2, suppl. 1, p. 37).*
DeJong et al (International Journal of Nanomedicine, 2008, vol. 3, pp. 133-149).*
Abstract of Ziemys et al, Tissue Barriers, 2015.*
Lunt et al, BMC Cancer, 2008, vol. 8, pp. 1-14.*
Muldoon et al, Journal of Clinical Oncology, 2007, vol. 25, pp. 2295-2305.*
Bertin et al, Cancer Letters, 2010, vol. 298, pp. 264-272.*
Gahan, Infectious Disorders Drug Targets, 2012, vol. 12, pp. 360-370.*
Hayashi et al, Oncology Reports, 2014, vol. 32, pp. 1815-1819.*
Cameron et al, (European Journal of Cancer, 2001, vol. 37, pp. 1545-1553).*
McCart-Reed et al, Breast Cancer Research, 2015, vol. 17, pp. 12 (11 pages).*
EP Search Report for EP Application No. 13169783, dated Aug. 30, 2013.
Gahan, P.B. et al., "The virtosome—a novel cytosolic informative entity and intercellular messenger", Cell Biochemistry and Function., vol. 28, No. 7, (Oct. 12, 2818), pp. 529-538.
Peters, D. et al., "Continuous adaptation through genetic communication—a putative role for cell-free DNA", Expert Opinion on Biological Therapy, Informa Healthcare, UK, vol. 12, No. suppl. 1, (Jun. 1, 2812), pp. S127-S131.

* cited by examiner

*Primary Examiner* — Karen Canella
(74) *Attorney, Agent, or Firm* — Nixon & Vanderhye PC

(57) ABSTRACT

The present invention concerns a pharmaceutical composition comprising virtosomes isolated from non-dividing cells or the medium in which the cells are grown, for use in the inhibition of tumor growth and/or prevention of metastases.

6 Claims, No Drawings

METHOD FOR BLOCKING TUMOUR GROWTH

This application claims priority to EP Application No. 13169783.1, filed on May 29, 2013, the entire content of which is hereby incorporated by reference.

TECHNICAL FIELD

The present invention relates to a new method for reducing or blocking tumour growth and preventing the spread of tumours in animal systems, in vivo.

BACKGROUND OF THE INVENTION

Studies on a range of prokaryote and eukaryote cells, tissues and whole organisms have shown that a newly synthesized DNA/RNA-lipoprotein complex is released from living cells but not from dying or dead cells (1-8). DNA-dependent DNA polymerase and DNA-dependent RNA polymerase are present amongst the proteins (9-14). The complex is a novel cytosolic component of eukaryote cells that is released in a regulated manner and has been named the virtosome (15).

The DNA of the virtosome ($3-5 \times 10^5$ daltons) forms ca 5% of the total virtosomal complex and is synthesised in the nucleus, possibly involving the DNA synthetic system described for extra-chromosomal circular DNA (16). The DNA appears to be similar in both cytosolic and released virtosomes. It is released into the cytosol where it appears ca 3 h later (17). Due to the size of the DNA, it may not leave the nucleus via the nuclear pores but may adopt an alternative route proposed for mRNP nuclear export (18). In the cytosol, the DNA combines with newly synthesised proteins, lipids and RNA prior to being released from the cell 3-5 h later (7, 8, 17, 19, 20). The RNA forms about half of the virtosomal components with protein forming about 40% (21). Experiments with chick embryo fibroblast (CEF) virtosomes released into the culture medium and allowed to enter fresh CEF cells showed that the released and the re-entered virtosomes isolated from the cytosol of the recipient cells were collected at the same point after agarose gel chromatography (22). This implied that membrane was neither gained nor lost on either exit from or entry to cells and that there was not a classical membrane associated with the virtosomes (7, 8, 17, 19, 20). This was confirmed by the phospholipid analyses of virtosomes showing them to have phosphatidylcholine levels too low for the presence of a standard membrane (21).

The released virtosome acts as an intercellular messenger that readily enters other cells where it can modify the biology of the recipient cells (15). Such modifications include immunological changes (23,24), the transformation of normal cells into tumour cells (25) and inhibition of DNA synthesis (26, 27). Virtosomes are able to enter cells without being digested by the lysosomal system. It is not clear how this is achieved. It could be by inhibiting the modification of lysosomal pH as has already been demonstrated for other systems (28), or it could bypass the lysosomal system as has been demonstrated for other DNA structures. Here it is possible that the virtosomal phosphatidylinositol plays a role (28-31).

The transformation of normal cells into tumour cells via released tumour DNA sequences has been demonstrated (25). Thus, the SW480 cell line, originating from a human colon carcinoma, presented a point mutation of the K-ras gene on both alleles. These cells in culture released the DNA-complex containing the mutated K-ras gene (Kirsten rat sarcoma viral oncogene homologue). When crude SW480 cell supernatant was given to NIH-3T3 cells, without the addition of any other compound, transformed foci appeared as numerously as those occurring after a transfection provoked by a clonal K-ras gene administered as a calcium precipitate. The presence of a mutated K-ras gene in the transfected foci of the NIH-3T3 cells was checked by hybridization after PCR. This result was confirmed by sequencing the PCR product (25).

Once a tumour has been detected it is important to be able to (i) block the further growth of the tumour, (ii) reduce tumour size and (iii) prevent the development of possible metastases. (i) and (iii) are currently treated either directly by either radiotherapy or chemotherapy or by surgery followed by chemotherapy/radiotherapy.

Normally, the virtosomes act primarily within a given tissue within the whole organism. Thus, such virtosomes released from non-dividing cells e.g. hepatocytes within the liver, will be unlikely to interact directly with tumour cells.

SUMMARY OF THE INVENTION

This invention exploits the messenger ability of the virtosomes to modify the biology of the recipient cells, and in particular, the ability of the virtosomes from non-dividing cells to block DNA synthesis in recipient dividing tumour cells. This, in turn, leads to a block on the development of tumours, their possible reduction in size and prevention of metastases.

The term "virtosomes from non-dividing cells" concerns the virtosomes from any type of non-dividing cell.

The term "tumour" concerns any type of tumour e.g. colorectal, liver and lung tumours.

The present invention concerns a pharmaceutical composition comprising virtosomes isolated from non-dividing cells or the medium in which the cells are grown, for use in the inhibition of tumour growth and/or prevention of metastases.

The non-dividing cells may be non-dividing lymphocytes, preferably said lymphocytes are T and/or B lymphocytes.

The non-dividing cells may also be non-dividing hepatocytes or non-dividing stem cells.

The virtosomes may be an active extract from non-dividing cells.

The pharmaceutical composition may be administered intravenously by direct intravenous injection of isolated virtosomes from non-dividing cells/tissues. In this case, the virtosomes may be encapsulated by liposomes or nanoparticles that may be tumour-targeted by attaching markers specific for the particular tumour. The intravenous treatment may need to be repeated at regular time intervals.

Thus, although the epithelial cells of healthy blood vessels are linked together by tight junctions that block the exit of large particles from the blood, tumour blood vessel epithelia are more leaky and permit liposomes of less than 400 nm to pass from the blood into the tumour. Normal vessels do not permit this exchange. Hence anti-cancer drugs can be targeted to tumours via liposomes (32). It is proposed that the either the complete virtosomes or active virtosomal components may be encapsulated by liposomes for targeting to the tumour. Virtosomes may also be carried by tumour-targeted nanoparticles (33).

In another embodiment, the invention relates to a method for isolating the virtosomes from the cell environment or the cytosol of the non-dividing cells comprising the steps of:

applying a high speed centrifugation, applying an agarose gel chromatography or a density gradient centrifugation.

In a further embodiment, the invention concerns a method for treatment of tumour growth in a mammal comprising administering to the mammal an effective amount of a pharmaceutical composition comprising virtosomes isolated from non-dividing cells or the medium in which the cells are grown.

The mammal may be a human that suffers from cancer.

DETAILED DESCRIPTION OF THE INVENTION

A more detailed description of example embodiments of the invention will now be given.

Preparation of the Virtosomes

The virtosomes are prepared from any non-dividing cells or tissues either in its newly synthesised form in the cytosol or after its spontaneous release from cells. The following example will demonstrate the retention of biological activity by the virtosomes isolated from either the cell environment (e.g. culture medium) or the cytosol. Freshly isolated mouse spleen lymphocytes are cultured at a concentration of $5 \times 10^6$ cells for 16 h overnight at 37.5° C. in 100 ml of RP MI 1640 medium (88 ml) containing CPSR-2 (10 ml), 10% gentamycin (0.8 ml) and 200 mM glutamine (1.2 ml) as a settling-in period. The cells are then separated by gentle centrifugation followed by re-suspension and re-incubation.

The medium containing the virtosomes is made by seeding lymphocytes at a concentration of $3 \times 10^6$ ml$^{-1}$ in 100 ml of RPMI medium 1640 (88 ml)+10% CPRS-2 (10 ml), 10% gentamycin (0.8 ml) and 200 mM glutamine (1.2 ml) at 37.5° C. and removing them after 8 h by centrifugation at 500 g for 10 min. The supernatant is further centrifuged at $1.2 \times 10^5$ g for 1 h in a preparation centrifuge.

The preparation of the virtosomes from the cytosol of either any cell type e.g. lymphocytes (26) or any tissue e.g. liver (26) is made by gently breaking the cells/tissues open in a serum-free medium using a Tenbrock glass homogeniser (10 up-and-down gentle passes) with a Teflon pestle. The resultant homogenate is centrifuged at 500 g for 10 min. The supernatant is further centrifuged at $1.2 \times 10^5$ g for 1 h in an ultracentrifuge (26). Only the virtosomes of the cytosolic particles are not pelleted after ultracentrifugation.

Isolation of the virtosomes after ultracentrifugation from either supernatant is achieved by agarose gel chromatography. Agarose gel columns (48 cm long×2.5 cm diameter) with an exclusion limit of $1.5 \times 10^6$ daltons are equilibriated with phosphate buffered saline (pH 7.4).

Two ml of the ultra-centrifuged medium are loaded onto the column and eluted by gravity flow with the same buffer (30 ml h$^{-1}$ flow rate). Of the 50 fractions collected, fractions 32-42 contain the eluted virtosomes from either source. The void volume is determined with blue dextran and serum albumin is used to determine the molecular weight elution pattern.

The virtosomes may also be prepared by filtration of the supernatant from ultracentrifugation through a Millipore bacterial filter of pore size 0.2 µm. Alternatively, the virtosomes may be separated by density gradient centrifugation using e.g. sucrose (7) or caesium chloride gradients (1).

In Vitro Assay

The purified virtosomes are tested for the retention of biological activity after purification. Thus, either the cytosolic or the culture medium derived virtosomes purified from either non-stimulated mouse lymphocytes or mouse liver are tested against a culture of mouse tumour cell line J774. As a control, the virtosomes from cells of tumour cell lines J774 and P497 are similarly prepared and tested against the tumour cell line J773 cells. The sterilized solutions are added to the cell cultures so forming 20% of the final cell incubation medium.

The results indicate that neither the J774 nor the P497 virtosomes have an effect upon the J774 cells.

However, the virtosomes isolated from the non-stimulated lymphocyte result in a reduction of J774 DNA synthesis and hence cell replication, by almost 70% whilst the liver cytosolic virtosomes yield an inhibition of approximately 60% (26). However, J774 and the P497 virtosomes have little effect (10-15%) on normal dividing 3T3 fibroblasts.

In addition, the tumour cell line SW480 co-cultured with virtosomes from non-dividing hepatocytes for 24 h showed a reduction of cell replication of more than 80%.

A similar experiment with HT1080, a fibrosarcoma cell line, showed a reduction of about 90% after 24 h treatment. Without further treatment, the remaining cells were able to divide and so escape the effects of the virtosomes. Moreover, when virtosomes were introduced into a 4-day culture of HT1080 cells where the cell numbers had reached to between 100,000 to 150,000, the addition of hepatic virtosomes reduced the cells number by three to seven times depending upon the concentration of the virtosomes added.

Human non-stimulated lymphocyte virtosomes also block cell division in stimulated lymphocytes (27).

In Vivo Assay

The virtosomes so produced from non-dividing cell populations (either from cultures or tissues) are injected intravenously into the tumour-bearing rats. This can involve virtosomes that have been prepared from the tumour bearer's own cells/tissues.

Thus, transfer of the application of virtosomal inhibition of tumour cell replication in vitro to an in vivo model was achieved after confirming that virtosomal preparations from non-dividing hepatocytes had no effect upon the rat strain BDIX employed. Daily intravenous injection was made for 10 consecutive days of non-dividing hepatocyte virtosomes into BDIX male rats that had been previously inoculated with DHD/K12-PROb cells in order to induce the formation of a tumour similar to colon adenocarcinoma. The presence of the virtosomes limited tumour development for the following 14 days, the tumours being either partially or completely reduced in size. As has been mentioned for the in vitro tumour cell cultures, the tumours reduced in size will require additional virtosomal treatment to reduce them further.

The examples and embodiments given in the present application are, of course, only for illustrative purposes and should not be considered in a limiting fashion. Other variants using equivalent means are of course possible as well without imparting from the spirit a scope of the present invention. In particular, other applications may be envisaged in the frame of the present invention and different embodiments may also be combined.

REFERENCES

1. Stroun, M. & Anker, P. (1972) Nucleic acids spontaneously released by living frog auricles. Biochem J 128: 100-101.

2. Stroun, M. & Anker, P. (1972) In vitro synthesis of DNA spontaneously released by bacteria or frog auricles. Biochimie 54: 1443-1452.
3. Anker, P. Stroun, M. & Maurice, P. (1975) Spontaneous release of DNA by human blood lymphocytes as shown in an in vitro system. Cancer Res 354: 2375-2382.
4. Anker, P. & Stroun, M. (1977a) The release of newly synthesized DNA from frog auricles. Arch Sci Genève 30: 230-241.
5. Stroun, M. Anker, P., Gahan, P. B. & Henri, J. (1977b) Spontaneous release of newly synthesized DNA from frog auricles. Arch Sci Geneva 30: 229-241.
6. Stroun, M., Anker, P., Beljanski, M., Henri, J., Lederrey, C., Ojha, 0. & Maurice, P. (1978) Presence of RNA in the nucleoprotein complex spontaneously released by human lymphocytes and frog auricles in culture. Cancer Res 38: 3546-3554.
7. Adams, D. H. & Gahan, P. B. (1982) Stimulated and non-stimulated rat spleen cells release different DNA complexes. Differentiation 22: 47-52.
8. Adams, D. H. & Gahan, P. B. (1983) The DNA extruded by rat spleen cells in culture. Int J Biochem 15: 547-552.
9. Stroun, M., Gahan, P. B. & Sarid, S. (1969) Agrobacterium tumefaciens RNA in non-tumorous cells. Biochem Biophys Res Commun 37: 652-657.
10. Stroun, M. (1971) On the nature of the polymerase responsible for the transcription of released bacterial DNA in plants. Biochem Biophys Res Commun 44: 571-578.
11. Stroun, M., Anker, P. Gahan, P., Rossier, A. & Greppin H. (1971) Agrobacterium tumefaciens ribonucleic acid synthesis in tomato cells and crown gall induction. J Bacteriol 106: 634-639.
12. Anker, P. & Stroun, M. (1972) Bacterial ribonucleic acid in the frog brain after bacterial peritoneal infection. Science 178: 621-623.
13. Anker, P., Stroun, M. & Maurice, P. (1976) Spontaneous extracellular synthesis of DNA released by human blood lymphocytes. Cancer Res 36: 2831-2839.
14. Anker, P. & Stroun, M. (1977) Spontaneous extracellular synthesis of DNA released by frog auricles. Arch Sci Genève 30: 263-278.
15. Gahan, P. B. & Stroun, M. (2010) The virtosome, a novel cytosolic informative entity and intercellular messenger. Cell Biochem Funct 28: 1-10.
16. Cohen, Z., Bacharach, E. & Lavi, S. (2006) Major mouse satellite DNA is prone to eccDNA formation via DNA ligase IV-dependent pathway. Oncogene 25:4515-4524.
17. Adams, D. H. & Macintosh, A. A. G. (1985) Studies on the cytosolic DNA of chick embryo fibroblasts and its uptake by recipient cultured cells. Int J Biochem 17: 1041-1051.
18. Speese, S. D., Ashley, J., Johki, V., et al. Nuclear envelope budding enables large ribonucleoprotein particle export during synaptic Wnt signaling. (2012) Cell 149: 832-846.
19. McIntosh, A. A. G. & Adams, D. H. (1985) Further studies of the extrusion of cytosol macromolecules by cultured chick embryo fibroblasts cells. Internat J Biochem 17: 147-153.
20. Challen, C. & Adams, D. H. (1987) The assembly of the DNA complex present in chick embryo cell cytosol. Internat J Biochem 19: 235-243. 20.
21. Viola-Magni, M. P. (2011) The biochemical composition of virtosomes. J Nucleic acids Invest 2 (Suppl 1):10.
22. Challen, C. & Adams, D. H. (1986) Further studies on the size and composition of chick embryo fibroblast cytosolic DNA complex. Int J Biochem 18: 423-429.
23. Anker, P., Jachertz, S., Maurice, P. A. & Stroun, M. (1984) Nude mice injected with DNA released by antigen by antigen stimulated human T lymphocytes produce specific antibodies expressing human characteristics. Cell Biochem Function 1: 33-37.
24. Anker, P., Jachertz, D., Stroun, 0., Brogger, R., Lederrey, C., Henri, J. & Maurice, P. (1989) The role of extracellular DNA in the transfer of information from T to B human lymphocytes in the course of an immune response. J Immunogenet 6: 475-481.
25. Anker, P., Lyautey J., Lefort, F., Lederrey, C. & Stroun, M (1994) Transformation of 3T3 cells and SW 480 cells displaying K-ras mutation. C.R. Acad. Sci. 10: 869-74.
26. Adams, D. H., Diaz, N. & Gahan, P. B. (1997) In vitro stimulation tumour cell media of [3H]thymidine incorporation by mouse spleen lymphocytes. Cell Biochem Function 15: 119-124.
27. Viola-Magni, M. P., Sesay, A., Cataldi, S., Gahan, P. B. & Stroun, M. (2011) Biological activity of virtosomes released by stimulated and non-stimulated lymphocytes. J. Nucleic Acids Invest 2: Suppl.1 p 37.
28. Trombone, A. P. F., Silva, C. L., Lima, K. M., Oliver, C., Jamur, M. C., Prescott, A. R. & Coelho-Castelo, A. A. M. (2007) Endocytosis of DNA-Hsp65 Alters the pH of the Late Endosome/Lysosome and Interferes with Antigen Presentation. PLoS ONE2 (9):e923.doi:10.1371/journal.pone.0000923.
29. Wolff, J. A., Malone, R. W., Williams, P., Chong, W., Acsadi, G., Jani, A. & Felgner, P. L, (1990) Direct gene transfer into mouse muscle in vivo. Science 247, 1465-1468.
30. Basner-Tschakarjan, E., Mirmohammadsadegh, A., Baer, A. & Hengge, U. R. (2004) Uptake and trafficking of DNA in keratinocytes: evidence for DNA-binding proteins. Gene Therapy 11, 765-774.
31. Haegle, H., Allam, R., Pawar, R. D. & Anders, J-H. (2009) Double-stranded RNA activates type I interferon secretion in glomerular endothelial cells via retinoic acid-inducible gene (RIG)-1. Nephrology Dialysis Transplantation doi: 10.1093/ndt/gfp339.
32. Zhang, L., Gu, F. X., Chan, J. M., Wang, A. Z., Langer, R. S. & Farokhzad, O. C. (2008). Nanoparticles in Medicine: Therapeutic Applications and Developments. Clinical Pharmacology and Therapeutics 83, 761-69.
33. De Jong, W. H. & Borm, P. J. A. (2008) Drug delivery and nanoparticles: Applications and hazards. Int. J. Nanomedicine 3, 133-149.

The invention claimed is:

1. A pharmaceutical composition comprising virtosomes isolated from non-dividing cells or the medium in which the cells are grown, wherein said virtosomes are encapsulated by liposomes; for use in the inhibition of tumour growth and/or prevention of metastases.

2. Pharmaceutical composition according to claim 1, wherein said non-dividing cells are non-dividing lymphocytes.

3. Pharmaceutical composition according to claim 2, wherein said non-dividing lymphocytes are T and/or B lymphocytes.

4. Pharmaceutical composition according to claim 1, wherein said non-dividing cells are non-dividing hepatocytes or non-dividing stem cells.

5. Pharmaceutical composition according to claim 1, wherein said virtosomes are an active component of the composition, wherein activity is reduction of tumour cell division and replication.

6. Pharmaceutical composition according to claim 1, wherein said composition is suitable for intravenous injection.

\* \* \* \* \*

UNITED STATES PATENT AND TRADEMARK OFFICE
CERTIFICATE OF CORRECTION

PATENT NO. : 9,555,075 B2
APPLICATION NO. : 14/290094
DATED : January 31, 2017
INVENTOR(S) : Garcia-Olmo et al.

Page 1 of 1

It is certified that error appears in the above-identified patent and that said Letters Patent is hereby corrected as shown below:

On the Title Page

(71) Applicants should read: The Foundation for Biomedical Research of La Paz University Hospital (FIBHULP), Madrid (ES); Peter Brian Gahan, London (GB); Maurice Stroun, Geneva, (CH)

(73) Assignees should read: THE FOUNDATION FOR BIOMEDICAL RESEARCH OF LA PAZ UNIVERSITY HOSPITAL (FIBHULP), Madrid (ES); Peter Brian GAHAN, London (GB); Maurice STROUN, Geneva, (CH)

Signed and Sealed this
Twenty-seventh Day of March, 2018

Andrei Iancu
*Director of the United States Patent and Trademark Office*